(12) United States Patent
Noguchi (10) Patent No.: US 11,918,417 B2
(45) Date of Patent: Mar. 5, 2024

(54) ULTRASOUND PROBE

(71) Applicant: FUJIFILM Corporation, Tokyo (JP)

(72) Inventor: Shinsuke Noguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 54 days.

(21) Appl. No.: 17/155,280

(22) Filed: Jan. 22, 2021

(65) Prior Publication Data

US 2021/0137495 A1    May 13, 2021

Related U.S. Application Data

(63) Continuation of application No. PCT/JP2019/028515, filed on Jul. 19, 2019.

(30) Foreign Application Priority Data

Jul. 25, 2018  (JP) ................................ 2018-139239

(51) Int. Cl.
*A61B 8/00* (2006.01)

(52) U.S. Cl.
CPC .......... *A61B 8/4455* (2013.01); *A61B 8/4472* (2013.01); *A61B 8/4494* (2013.01); *A61B 8/56* (2013.01)

(58) Field of Classification Search
CPC ... A61B 8/4455; A61B 8/4472; A61B 8/4494; A61B 8/56; A61B 2050/3014;
(Continued)

(56) References Cited

U.S. PATENT DOCUMENTS

2008/0194960 A1*  8/2008  Randall .................... A61B 8/00
                                                              600/459
2016/0317131 A1   11/2016  Schwartz Klessel et al.
(Continued)

FOREIGN PATENT DOCUMENTS

CN         103413901 B  *  3/2017
JP         S55-162184 U    11/1980
(Continued)

OTHER PUBLICATIONS

An Office Action; "Notice of Reasons for Refusal," mailed by the Japanese Patent Office dated Feb. 15, 2022, which corresponds to Japanese Patent Application No. 2020-532359 and is related to U.S. Appl. No. 17/155,280 with English language translation.
(Continued)

*Primary Examiner* — Colin T. Sakamoto
*Assistant Examiner* — Tommy T Ly
(74) *Attorney, Agent, or Firm* — Studebaker & Brackett PC (57) ABSTRACT

An ultrasound probe 11 includes a transducer array 15, a housing body 13 having a battery accommodation portion 18, a battery 16 that is accommodated in the battery accommodation portion 18, a battery cover 14 that is attachably and detachably mounted on the housing body 13 to cover the battery accommodation portion 18 and has a cover rib CL1 protruding toward the battery accommodation portion 18, and an elastically deformable waterproof packing P1 that is disposed between a side surface of the cover rib CL1 and the housing body 13. The waterproof packing P1 is elastically compressed between the side surface of the cover rib CL1 and the housing body 13, and restrains water from entering the battery accommodation portion 18 from between the housing body 13 and the battery cover 14.

12 Claims, 8 Drawing Sheets

(58) Field of Classification Search
CPC .. H04M 1/0262; G06F 1/1635; G06F 1/1656; G06K 19/0706
See application file for complete search history.

(56) References Cited

U.S. PATENT DOCUMENTS

2018/0077793 A1* 3/2018 Qian ................... H01R 12/775
2018/0353153 A1* 12/2018 Huang ................. A61B 8/4472

FOREIGN PATENT DOCUMENTS

| JP | 3168946 B2 | * | 5/2001 |
|----|------------|---|--------|
| JP | 2008-288174 A | | 11/2008 |
| JP | 2010-182603 A | | 8/2010 |
| JP | 2013-247016 A | | 12/2013 |
| JP | 2014057165 A | * | 3/2014 |
| JP | 2015103869 A | * | 6/2015 |
| JP | 2015-211726 A | | 11/2015 |
| JP | 2016-209569 A | | 12/2016 |
| JP | 2018032834 A | * | 3/2018 |

OTHER PUBLICATIONS

International Search Report issued in PCT/JP2019/028515; dated Oct. 15, 2019.
International Preliminary Report On Patentability and Written Opinion issued in PCT/JP2019/028515; dated Jan. 26, 2021.
An Office Action; "Notice of Reasons for Refusal," mailed by the Japanese Patent Office dated May 16, 2023, which corresponds to Japanese Patent Application No. 2022-139306 and is related to U.S. Appl. No. 17/155,280; with English language translation.

* cited by examiner

ULTRASOUND PROBE

CROSS-REFERENCE TO RELATED APPLICATIONS

This application is a Continuation of PCT International Application No. PCT/JP2019/028515 filed on Jul. 19, 2019, which claims priority under 35 U.S.C. § 119(a) to Japanese Patent Application No. 2018-139239 filed on Jul. 25, 2018. Each of the above applications is hereby expressly incorporated by reference, in its entirety, into the present application.

BACKGROUND OF THE INVENTION

1. Field of the Invention

The present invention relates to an ultrasound probe, and in particular, to an ultrasound probe that is connected to a diagnostic apparatus body through wireless communication.

2. Description of the Related Art

Hitherto, in a medical field, an ultrasound diagnostic apparatus using an ultrasound image has come into practical use. In general, this kind of ultrasound diagnostic apparatus has an ultrasound probe that incorporates a transducer array, and an apparatus body connected to the ultrasound probe. The ultrasound probe transmits ultrasonic waves toward a subject and receives ultrasound echoes from the subject, and the apparatus body electrically processes reception signals to generate an ultrasound image.

In recent years, for example, as disclosed in JP2015-211726A, a wireless ultrasound probe that is connected to a diagnostic apparatus body through wireless communication has been developed.

Such a wireless ultrasound probe transmits reception signals output from the transducer array to the diagnostic apparatus body through wireless communication or incorporates a circuit that performs signal processing, executes digital processing on the reception signals output from the transducer array, and transmits the reception signals to the diagnostic apparatus body through the wireless communication. The diagnostic apparatus body generates and displays an ultrasound image based on the signals transmitted from the ultrasound probe in a wireless manner.

SUMMARY OF THE INVENTION

In general, the wireless ultrasound probe disclosed in JP2015-211726A incorporates a battery as a drive power supply in many cases. It is desirable that such a battery is disposed to be replaceable from a viewpoint of maintenance or the like. However, normally, in order to restrain water from entering the inside of the ultrasound probe from the outside, a housing is sealed using an adhesive to close the inside of an ultrasound probe in many cases. In a case where the inside of the ultrasound probe is closed using the adhesive, there is a problem in that the battery incorporated in the ultrasound probe cannot be replaced.

The invention has been accomplished in order to solve such a problem of the related art, and an object of the invention is to provide an ultrasound probe capable of disposing a battery to be replaceable while securing a waterproof property for the battery.

In order to achieve the above-described object, an aspect of the invention provides an ultrasound probe comprising a transducer array, a housing body having a battery accommodation portion, a battery that is accommodated in the battery accommodation portion of the housing body, a battery cover that is attachably and detachably mounted on the housing body to cover the battery accommodation portion and has a cover rib protruding toward the battery accommodation portion, and an elastically deformable waterproof packing that is disposed between a side surface of the cover rib of the battery cover and the housing body, in which the waterproof packing is elastically compressed between the side surface of the cover rib and the housing body, and restrains water from entering the battery accommodation portion from between the housing body and the battery cover.

It is preferable that the cover rib has a closed shape extending along a whole periphery of the battery accommodation portion, and the waterproof packing is disposed along a whole periphery of the cover rib.

In this case, it is preferable that the battery accommodation portion has a battery fixing surface to which the battery is fixed, and a sidewall that protrudes from the battery fixing surface toward the battery cover, and the waterproof packing is elastically compressed between the side surface of the cover rib and the sidewall of the battery accommodation portion.

It is preferable that the sidewall has a closed shape extending along a whole periphery of the battery fixing surface to surround the battery fixing surface.

In this case, the cover rib may be disposed more inside the battery accommodation portion than the sidewall of the battery accommodation portion, and the waterproof packing may be elastically compressed between the side surface of the cover rib and an inner wall surface of the sidewall of the battery accommodation portion.

Alternatively, the cover rib may be disposed more outside the battery accommodation portion than the sidewall of the battery accommodation portion, and the waterproof packing may be elastically compressed between the side surface of the cover rib and an outer wall surface of the sidewall of the battery accommodation portion.

The battery may be fixed to the battery fixing surface by a double-sided tape.

It is preferable that the battery accommodation portion is a recess portion formed in the housing body, the battery fixing surface constitutes a bottom portion of the recess portion, and the sidewall of the battery accommodation portion constitutes a side portion of the recess portion.

The waterproof packing may be fixed to the side surface of the cover rib.

Alternatively, the waterproof packing may be fixed to the sidewall of the battery accommodation portion.

The housing body may have a prismatic or columnar shape extending along a center axis, and the transducer array may be disposed at one end of the housing body along the center axis.

In this case, the battery cover may extend in parallel with the center axis and may be disposed on a side surface of the housing body.

Alternatively, the battery cover may be disposed at the other end of the housing body along the center axis.

It is preferable that the waterproof packing is formed of silicone rubber or fluororubber.

According to the aspect of the invention, the ultrasound probe comprises the housing body having the battery accommodation portion, the battery that is accommodated in the battery accommodation portion of the housing body, the battery cover that is attachably and detachably mounted on the housing body to cover the battery accommodation portion and has the cover rib protruding toward the battery accommodation portion, and the elastically deformable waterproof packing that is disposed between the side surface of the cover rib of the battery cover and the housing body, in which the waterproof packing is elastically compressed between the side surface of the cover rib and the housing body, and restrains water from entering the battery accommodation portion from between the housing body and the battery cover. Thus, it is possible to dispose the battery to be replaceable while securing a waterproof property for the battery.

DESCRIPTION OF THE PREFERRED EMBODIMENTS

Hereinafter, embodiments of the invention will be described referring to the accompanying drawings.

Embodiment 1

Figure 1:
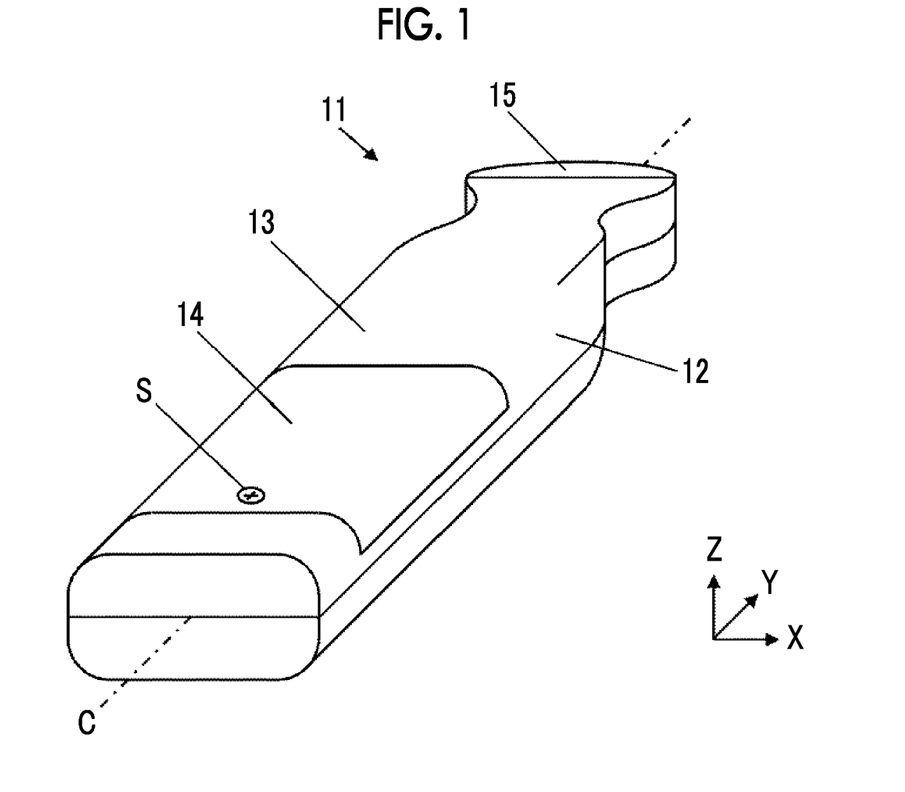
FIG. 1 is a perspective view of an ultrasound probe according to Embodiment 1 of the invention.

FIG. 1 shows an ultrasound probe 11 according to Embodiment 1 of the invention. As shown in FIG. 1, the ultrasound probe 11 has a housing 12 having a substantially prismatic shape around a center axis C, and the housing 12 has a housing body 13 and a battery cover 14 attached to a side surface of the housing body 13. The housing body 13 and the battery cover 14 are formed of, for example, an insulating resin material, such as modified polyphenylene ether (m-PPE) or polycarbonate/acrylonitrile butadiene styrene alloy (PC/ABS alloy).

In the example shown in FIG. 1, the battery cover 14 is attachably and detachably attached to the housing body 13 by a screw S. The ultrasound probe 11 has a transducer array 15 at one end of the housing body 13 along the center axis C.

Hereinafter, for description, a direction that is parallel to the center axis C and is directed toward the transducer array 15 is referred to as a +Y direction, a width direction perpendicular to the Y direction is referred to as an X direction, and a height direction perpendicular to the X direction and the Y direction is referred to as a Z direction.

As described below, the ultrasound probe 11 transmits and receives ultrasonic waves to and from a subject with the transducer array 15 to capture an ultrasound image representing a tomographic plane of the subject, and is connected to a diagnostic apparatus body, which generates and displays the ultrasound image based on signals acquired by the ultrasound probe 11, through wireless communication. As described below, the ultrasound probe 11 incorporates a battery, and electric power is supplied to each circuit of the ultrasound probe 11 by the incorporated battery.

Figure 2:
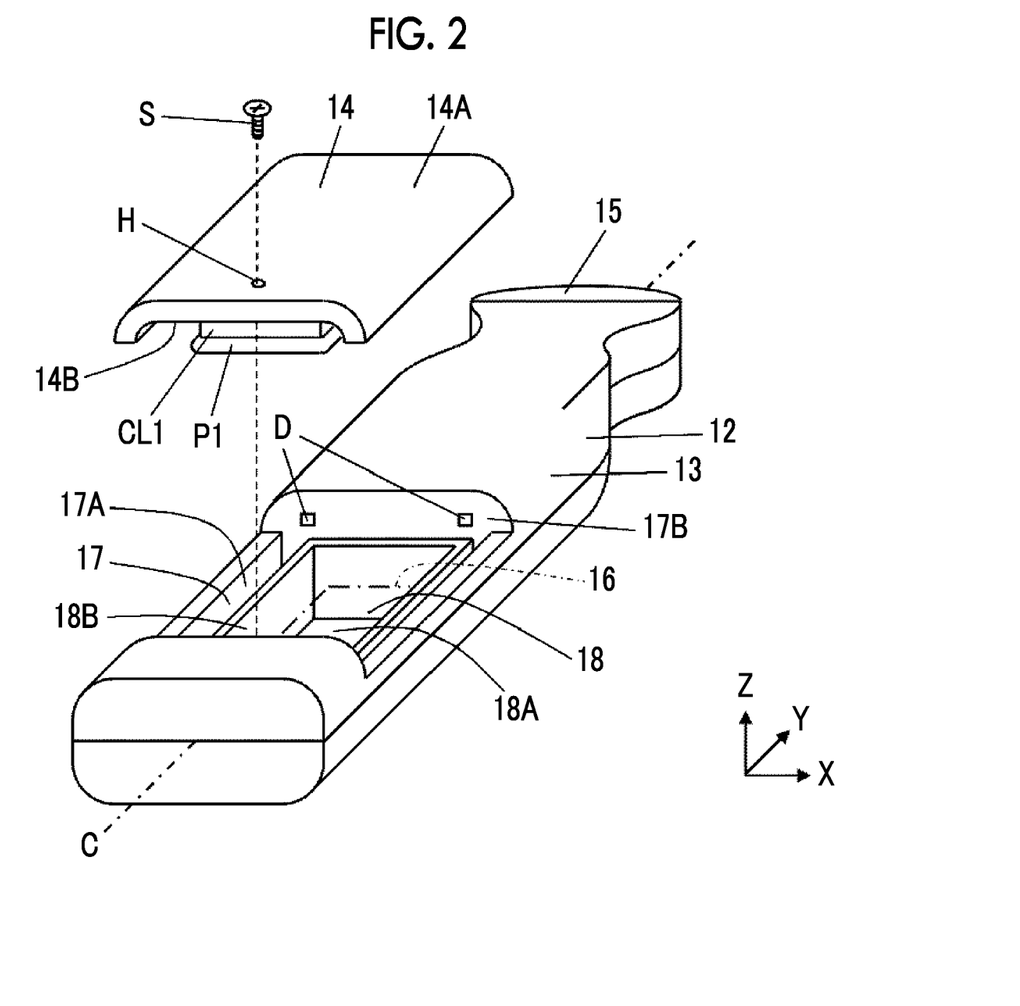
FIG. 2 is an exploded view of the ultrasound probe according to Embodiment 1 of the invention.

FIG. 2 is an exploded view of the ultrasound probe 11. As shown in FIG. 2, a recess portion 17 is formed in a side portion of the housing body 13, and the housing body 13 has a battery accommodation portion 18, which accommodates the battery 16, in the recess portion 17.

In the recess portion 17 of the housing body 13, a pair of first side portions 17A that extends in a direction parallel to the center axis C, that is, the Y direction and a pair of second side portions 17B that extends in the X direction are formed. In the second side portion 17B on the transducer array 15 side, that is, on a +Y direction side between a pair of second side portions 17B, a pair of insertion holes D into which hook portions of the battery cover 14 described below are inserted is formed. In a case where the hook portions of the battery cover 14 described below are inserted into a pair of insertion holes D, the battery cover 14 is fixed to the housing body 13.

The battery accommodation portion 18 of the housing body 13 has a battery fixing surface 18A which constitutes a bottom portion of the recess portion 17 and to which the battery 16 is fixed, and a sidewall 18B that protrudes from the battery fixing surface 18A toward the battery cover 14, that is, toward a +Z direction. The sidewall 18B of the battery accommodation portion 18 has a closed plate shape extending along the whole periphery of the battery fixing surface 18A, and has four sides of a pair of sides extending in the X direction and a pair of sides extending in the Y direction.

As shown in FIG. 2, both end portions of the battery cover 14 in the X direction are curved in a −Z direction, and the battery cover 14 has a cover upper surface 14A that constitutes a part of an outer surface of the housing 12, and a cover lower surface 14B that is directed in an opposite direction to the cover upper surface 14A. The battery cover 14 has a cover rib CL1 that protrudes in the −Z direction from the cover lower surface 14B toward the battery accommodation portion 18, and a waterproof packing P1 fixed to the cover rib CL1. The waterproof packing P1 is elastically deformable and is constituted of an elastic body. Here, since the ultrasound probe 11 is brought into contact with the subject for use, in general, the ultrasound probe 11 is disinfected by a chemical, such as isopropyl alcohol, glutaraldehyde, hypochlorous acid, or ethanol, in many cases. For this reason, it is preferable that the waterproof packing P1 is formed of silicone rubber, fluororubber, or the like having chemical resistance. The waterproof packing P1 can be formed integrally with the cover rib CL1, for example, by so-called insert molding. The waterproof packing P1 may be fixed to the cover rib CL1, for example, by an adhesive or the like.

In the battery cover 14, a through-hole H that passes therethrough in the Z direction is formed. Though not shown, in the housing body 13, a screw hole for fixing the screw S is formed at a position corresponding to the through-hole H of the battery cover 14, and the screw S is screwed into the screw hole of the housing body 13 in a state of being inserted into the through-hole H of the battery cover 14. Thereby, the battery cover 14 is fixed to the housing body 13.

Figure 3:
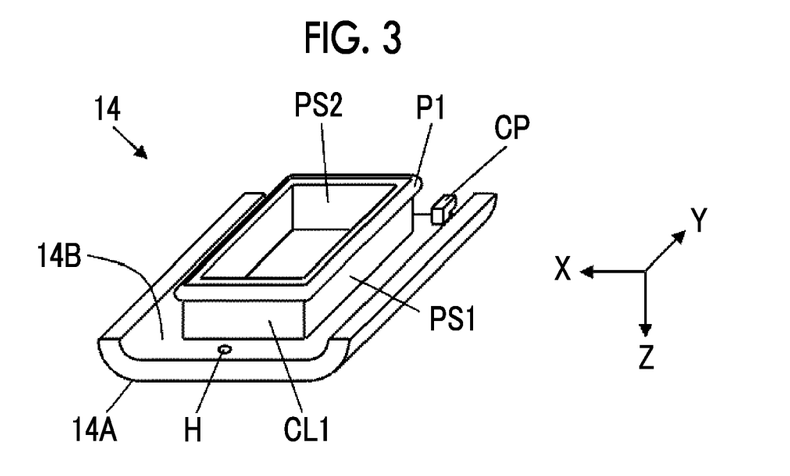
FIG. 3 is a perspective view of a battery cover as viewed from a rear side in Embodiment 1 of the invention.

As shown in FIG. 3, the cover rib CL1 of the battery cover 14 has a plate shape including four sides of a pair of sides extending in the X direction and a pair of sides extending in the Y direction. That is, The cover rib CL1 has a closed plate shape extending along the whole periphery of the battery accommodation portion 18 when the cover rib CL1 is attached to the housing body 13. The cover rib CL1 has an outer peripheral surface PS1 and an inner peripheral surface PS2, and the waterproof packing P1 is fixed over the whole periphery of the outer peripheral surface PS1. In an end portion of the cover lower surface 14B of the battery cover 14 in the +Y direction, a pair of hook portions CP is formed. A pair of hook portions CP is inserted into a pair of insertion holes D formed in the housing body 13 when the battery cover 14 is attached to the housing body 13.

Figure 4:
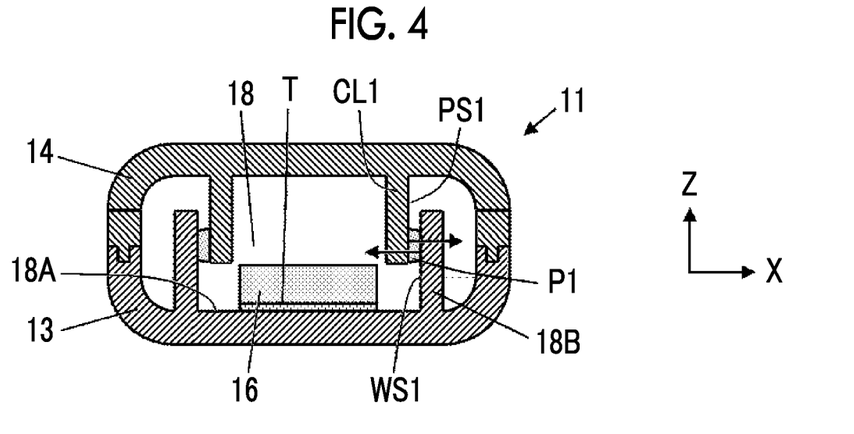
FIG. 4 is a cross-sectional view of the ultrasound probe according to Embodiment 1 of the invention.

A cross-sectional view of the ultrasound probe 11 taken in parallel with an XZ plane to pass through the battery cover 14 is shown in FIG. 4. As shown in FIG. 4, in a state in which the battery cover 14 is attached to the housing body 13, the cover rib CL1 of the battery cover 14 is disposed more inside the battery accommodation portion 18 than the sidewall 18B of the battery accommodation portion 18.

For this reason, for example, as shown in FIG. 4, in a cross section of the ultrasound probe 11 taken along the XZ plane, the waterproof packing P1 receives force in a +X direction and a −X direction and is elastically compressed between the outer peripheral surface PS1 of the cover rib CL1 and an inner wall surface WS1 of the sidewall 18B of the battery accommodation portion 18. Though not shown, in a cross section of the ultrasound probe 11 taken along a YZ plane, the waterproof packing P1 receives force in a +Y direction and a −Y direction and is elastically compressed between the outer peripheral surface PS1 of the cover rib CL1 and the inner wall surface WS1 of the sidewall 18B of the battery accommodation portion 18.

With this, with the ultrasound probe 11 according to Embodiment 1 of the invention, the waterproof packing P1 is closely attached to the inner wall surface WS1 of the sidewall 18B of the battery accommodation portion 18, and water is restrained from entering the battery accommodation portion 18 from between the housing body 13 and the battery cover 14.

In a case where force is applied to the battery cover 14 in an attachment and detachment of the battery cover 14 with respect to the housing body 13, that is, the Z direction, the battery cover 14 is bent in the Z direction, and there is a concern that a waterproof property to the battery accommodation portion 18 is degraded. In contrast, in the ultrasound probe 11 according to Embodiment 1 of the invention, a direction of force applied to the cover rib CL1 and the sidewall 18B of the battery accommodation portion 18 by the waterproof packing P1 is only the X direction and the Y direction. Thus, it is possible to restrain the battery cover 14 from being bent. For this reason, with the ultrasound probe 11 according to Embodiment 1 of the invention, it is possible to further improve a waterproof property to the battery accommodation portion 18.

From the above, with the ultrasound probe 11 according to Embodiment 1, the waterproof packing P1 is fixed to the outer peripheral surface PS1 of the cover rib CL1 formed in the battery cover 14 attachable and detachable to and from the housing body 13, and in a state in which the battery cover 14 is attached to the housing body 13, the waterproof packing P1 is elastically compressed between the outer peripheral surface PS1 of the cover rib CL1 and the inner wall surface WS1 of the sidewall 18B of the battery accommodation portion 18. Thus, it is possible to dispose the battery 16 to be replaceable while securing a waterproof property for the battery 16.

Figure 5:
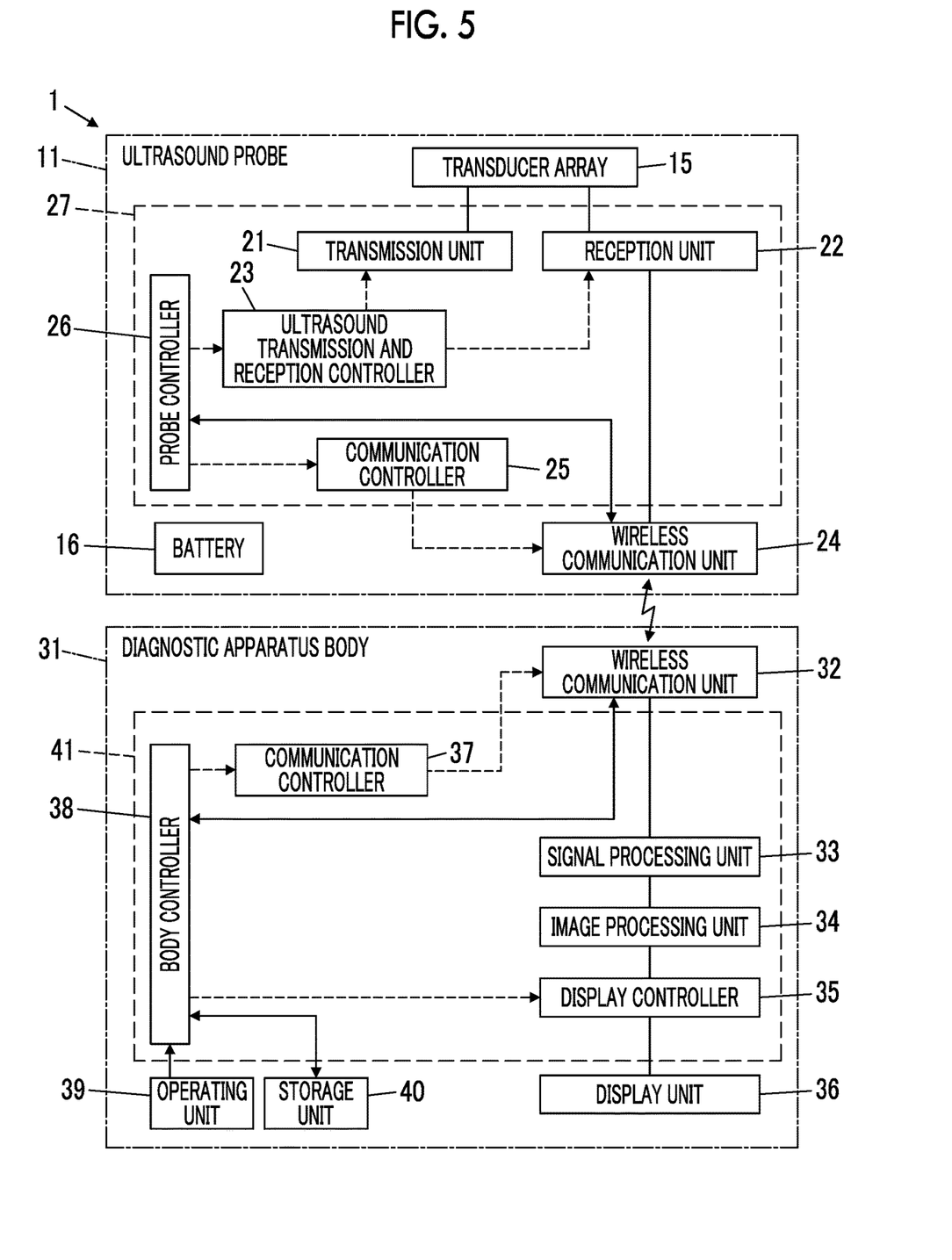
FIG. 5 is a block diagram showing the configuration of an ultrasound diagnostic apparatus comprising the ultrasound probe according to Embodiment 1 of the invention.

Next, an ultrasound diagnostic apparatus 1 comprising the ultrasound probe 11 according to Embodiment 1 of the invention will be described. FIG. 5 shows the configuration of the ultrasound diagnostic apparatus 1. As shown in FIG. 5, the ultrasound diagnostic apparatus 1 comprises the ultrasound probe 11 according to Embodiment 1 of the invention and a diagnostic apparatus body 31, and the ultrasound probe 11 and the diagnostic apparatus body 31 are connected through wireless communication.

The ultrasound probe 11 comprises the transducer array 15, and a transmission unit 21 and a reception unit 22 are connected to the transducer array 15. An ultrasound transmission and reception controller 23 is connected to the transmission unit 21 and the reception unit 22. A wireless communication unit 24 is connected to the reception unit 22, and a communication controller 25 is connected to the wireless communication unit 24. A probe controller 26 is connected to the ultrasound transmission and reception controller 23, the wireless communication unit 24, and the communication controller 25. Here, the wireless communication unit 24 and the probe controller 26 are connected in such a manner that information can be transferred in two directions. The ultrasound probe 11 incorporates the battery 16.

The transmission unit 21, the reception unit 22, the ultrasound transmission and reception controller 23, the communication controller 25, and the probe controller 26 constitute an ultrasound probe-side processor 27.

The diagnostic apparatus body 31 comprises a wireless communication unit 32, and a signal processing unit 33, an image processing unit 34, a display controller 35, and a display unit 36 are sequentially connected to the wireless communication unit 32. A communication controller 37 is connected to the wireless communication unit 32, and a body controller 38 is connected to the wireless communication unit 32, the communication controller 37, and the display controller 35. An operating unit 39 and a storage unit 40 are connected to the body controller 38. Here, the wireless communication unit 32 and the body controller 38, and the body controller 38 and the storage unit 40 are connected in such a manner that information can be transferred in two directions.

The signal processing unit 33, the image processing unit 34, the display controller 35, the communication controller 37, and the body controller 38 constitute a diagnostic apparatus body-side processor 41.

The wireless communication unit 24 of the ultrasound probe 11 and the wireless communication unit 32 of the diagnostic apparatus body 31 are connected in such a manner that information can be transferred in two directions.

With this, the ultrasound probe 11 and the diagnostic apparatus body 31 are connected through wireless communication.

The transducer array 15 of the ultrasound probe 11 shown in FIG. 5 has a plurality of transducers arranged in a one-dimensional or two-dimensional manner. The transducers transmit ultrasonic waves in compliance with drive signals supplied from the transmission unit 21, receive ultrasound echoes from the subject, and output reception signals. Each transducer is constituted by forming electrodes at both ends of a piezoelectric body formed of, for example, piezoelectric ceramic represented by lead zirconatetitanate (PZT), a polymer piezoelectric element represented by poly vinylidene di fluoride (PVDF), piezoelectric single crystal represented by lead magnesium niobate-lead titanate (PMN-PT), or the like.

The ultrasound transmission and reception controller 23 of the ultrasound probe-side processor 27 performs control such that the transmission unit 21 and the reception unit 22 perform transmission of an ultrasonic beam and reception of ultrasound echoes based on an instruction from the probe controller 26, respectively.

The transmission unit 21 of the ultrasound probe-side processor 27 includes, for example, a plurality of pulse generators, and adjusts a delay amount of each drive signal based on a transmission delay pattern selected according to a control signal from the ultrasound transmission and reception controller 23 such that ultrasonic waves transmitted from a plurality of transducers of the transducer array 15 form an ultrasonic beam, and supplies the drive signals to a plurality of transducers. In this way, in a case where a pulsed or continuous-wave voltage is applied to the electrodes of each of a plurality of transducers of the transducer array 15, the piezoelectric body expands and contracts to generate a pulsed or continuous-wave ultrasonic wave from each of the transducers. An ultrasonic beam is formed from a combined wave of the ultrasonic waves.

The transmitted ultrasonic beam is reflected by, for example, a target, such as a part of the subject, and propagates toward the transducer array 15 of the ultrasound probe 11. The ultrasound echoes that propagate toward the transducer array 15 in this way are received by the respective transducers constituting the transducer array 15. In this case, each of the transducers constituting the transducer array 15 expands and contracts with reception of the propagating ultrasound echo to generate an electrical signal, and outputs the electrical signal to the reception unit 22.

Figure 6:
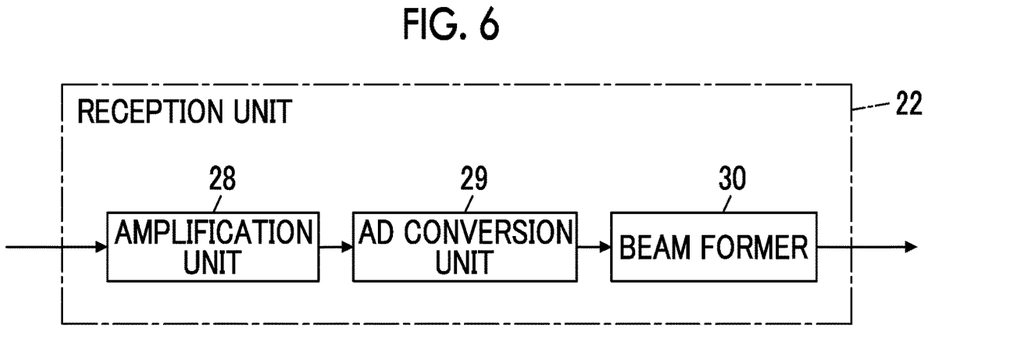
FIG. 6 is a block diagram showing the internal configuration of a reception unit in Embodiment 1 of the invention.

The reception unit 22 of the ultrasound probe-side processor 27 executes processing of the reception signals output from the transducer array 15 in compliance with a control signal from the ultrasound transmission and reception controller 23. As shown in FIG. 6, the reception unit 22 has a configuration in which an amplification unit 28, an analog-to-digital (AD) conversion unit 29, and a beamformer 30 are connected in series. The amplification unit 28 amplifies the reception signal input from each of the transducers constituting the transducer array 15 and transmits the amplified reception signal to the AD conversion unit 29. The AD conversion unit 29 converts the reception signal transmitted from the amplification unit 28 into digitized data and sends the digitized data to the beamformer 30. The beamformer 30 executes reception focus processing of giving a delay to each piece of data compliant with a set sound speed based on a reception delay pattern selected according to a control signal from the ultrasound transmission and reception controller 23 and performing addition (phasing addition). With the reception focus processing, a sound ray signal in which a focus of the ultrasound echo is narrowed on a given scanning line is generated. The sound ray signal generated in this manner is sent to the wireless communication unit 24 of the ultrasound probe 11.

The wireless communication unit 24 of the ultrasound probe 11 includes an antenna that performs transmission and reception of radio waves, and performs wireless communication with the wireless communication unit 32 of the diagnostic apparatus body 31. In this case, the wireless communication unit 24 modulates a carrier based on the sound ray signal sent from the reception unit 22 to generate a transmission signal and transmits the generated transmission signal to the wireless communication unit 32 of the diagnostic apparatus body 31 in a wireless manner. As a modulation system of the carrier, for example, amplitude shift keying (ASK), phase shift keying (PSK), quadrature phase shift keying (QPSK), 16 quadrature amplitude modulation (16QAM), or the like is used.

The communication controller 25 of the ultrasound probe-side processor 27 performs control such that the wireless communication unit 24 of the ultrasound probe 11 transmits the sound ray signal with transmission field intensity set by the probe controller 26.

The probe controller 26 of the ultrasound probe-side processor 27 performs control of each unit of the ultrasound probe 11 based on a program or the like stored in advance.

The battery 16 of the ultrasound probe 11 is incorporated in the ultrasound probe 11, and supplies electric power to each circuit of the ultrasound probe 11.

The wireless communication unit 32 of the diagnostic apparatus body 31 includes an antenna that performs transmission and reception of radio waves, and performs wireless communication with the wireless communication unit 24 of the ultrasound probe 11. In this case, the wireless communication unit 32 of the diagnostic apparatus body 31 outputs a sound ray signal, for example, by receiving the transmission signal transmitted from the wireless communication unit 24 of the ultrasound probe 11 through the antenna in a wireless manner and demodulating the received transmission signal. The wireless communication unit 32 of the diagnostic apparatus body 31 sends the sound ray signal output in this manner to the signal processing unit 33.

The signal processing unit 33 of the diagnostic apparatus body-side processor 41 performs correction of attenuation of the sound ray signal sent from the wireless communication unit 32 due to a propagation distance according to a depth of a reflection position of the ultrasonic wave, and then, executes envelope detection to generate a signal as tomographic image information regarding a tissue in the subject.

The image processing unit 34 of the diagnostic apparatus body-side processor 41 generates an ultrasound image signal by raster-converting the signal generated by the signal processing unit 33 into an image signal in compliance with a normal television signal scanning system and executing various kinds of necessary image processing, such as brightness correction, gradation correction, sharpness correction, and color correction, on the image signal generated in this manner. The image processing unit 34 sends the ultrasound image signal generated in this manner to the display controller 35.

The display controller 35 of the diagnostic apparatus body-side processor 41 executes predetermined processing on the ultrasound image signal generated by the image processing unit 34 and displays an ultrasound image on the display unit 36 under the control of the body controller 38.

The display unit 36 of the diagnostic apparatus body 31 displays an image under the control of the display controller 35, and includes, for example, a display device, such as a liquid crystal display (LCD), an organic electroluminescence display (organic EL display).

The communication controller 37 of the diagnostic apparatus body-side processor 41 performs control such that the wireless communication unit 32 of the diagnostic apparatus body 31 receives the transmission signal from the wireless communication unit 24 of the ultrasound probe 11.

The body controller 38 of the diagnostic apparatus body-side processor 41 performs control of each unit of the diagnostic apparatus body 31 based on a program stored in advance in the storage unit 40 or the like and a user's operation through the operating unit 39.

The operating unit 39 of the diagnostic apparatus body 31 is provided for the user to perform an input operation, and can comprise a keyboard, a mouse, a trackball, a touch pad, a touch panel, and the like.

The storage unit 40 of the diagnostic apparatus body 31 stores an operation program and the like of the diagnostic apparatus body 31, and as the storage unit 40, a recording medium, such as a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory), a server, or the like can be used.

Here, in the ultrasound probe 11, the ultrasound probe-side processor 27 having the transmission unit 21, the reception unit 22, the ultrasound transmission and reception controller 23, the communication controller 25, and the probe controller 26, and the diagnostic apparatus body-side processor 41 having the signal processing unit 33, the image processing unit 34, the display controller 35, the communication controller 37, and the body controller 38 are constituted of a central processing unit (CPU) and a control program causing the CPU to execute various kinds of processing. However, the ultrasound probe-side processor 27 and the diagnostic apparatus body-side processor 41 may be constituted using a field programmable gate array (FPGA), a digital signal processor (DSP), an application specific integrated circuit (ASIC), a graphics processing unit (GPU), or other integrated circuits (ICs) or may be constituted by combining the IC circuits.

The transmission unit 21, the reception unit 22, the ultrasound transmission and reception controller 23, the communication controller 25, and the probe controller 26 of the ultrasound probe-side processor 27 may be constituted to be partially or wholly integrated into one CPU or the like. The signal processing unit 33, the image processing unit 34, the display controller 35, the communication controller 37, and the body controller 38 of the diagnostic apparatus body-side processor 41 may be constituted to be partially or wholly integrated into one CPU or the like.

In Embodiment 1, as shown in FIG. 1, although the housing 12 and the housing body 13 have a substantially prismatic shape, the shapes of the housing 12 and the housing body 13 are not particularly limited. For example, the housing 12 and the housing body 13 may have a columnar shape.

In Embodiment 1, as shown in FIG. 2, although the sidewall 18B of the battery accommodation portion 18 has the four sides of a pair of sides extending in the X direction and a pair of sides extending in the Y direction, and has a closed shape surrounding the battery fixing surface 18A in a rectangular shape, the shape of the sidewall 18B of the battery accommodation portion 18 is not particularly limited. For example, the sidewall 18B of the battery accommodation portion 18 can have a closed shape surrounding the battery fixing surface 18A in a circular shape, a closed shape surrounding the battery fixing surface 18A in a polygonal shape, or a closed shape surrounding the battery fixing surface 18A in any other shapes. The sidewall 18B of the battery accommodation portion 18 may not have a shape continuously surrounding the battery fixing surface 18A. However, in order to improve a waterproof property, it is preferable that the sidewall 18B of the battery accommodation portion 18 has a closed shape continuously surrounding the battery fixing surface 18A.

The cover rib CL1 of the battery cover 14 can have any shape similarly to the sidewall 18B of the battery accommodation portion 18. However, in order to make the waterproof packing P1 be closely attached to the inner wall surface WS1 of the sidewall 18B of the battery accommodation portion 18, it is preferable that the cover rib CL1 has a shape along the sidewall 18B of the battery accommodation portion 18.

Figure 7:
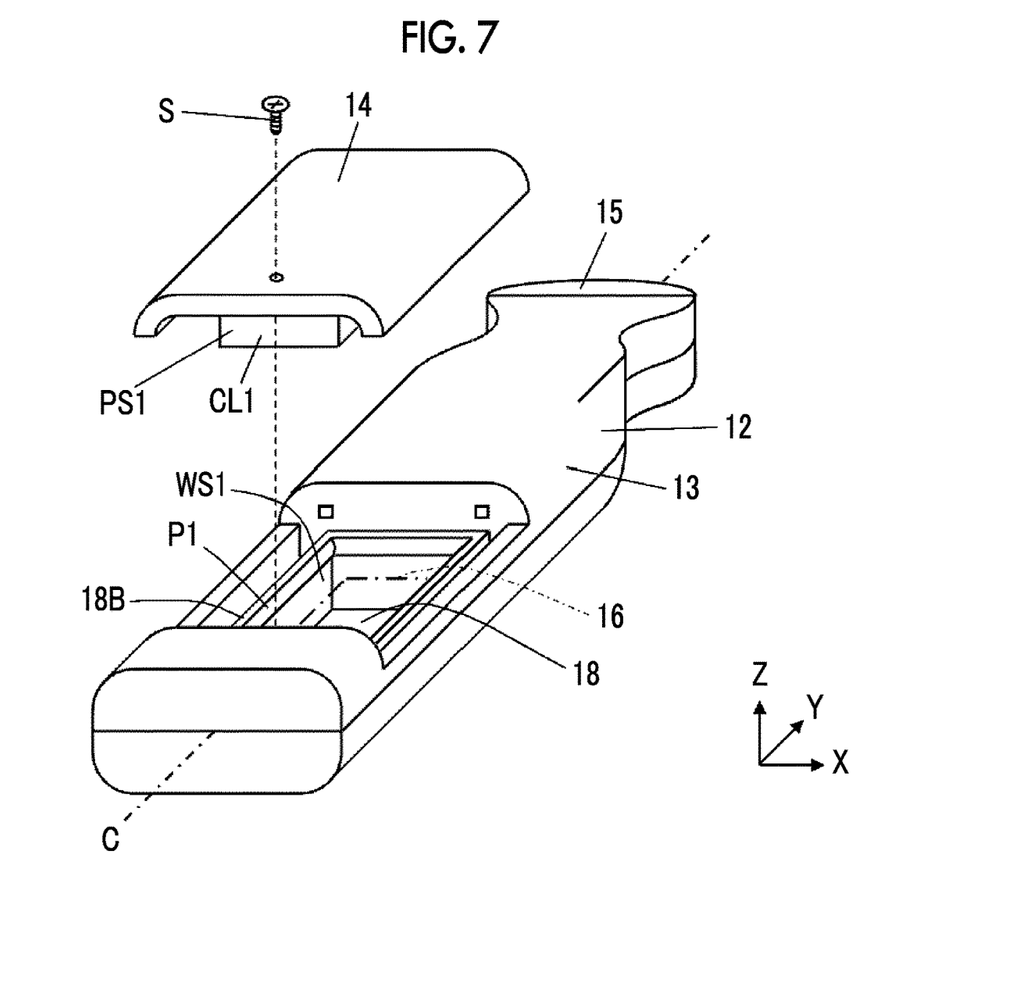
FIG. 7 is an exploded view of an ultrasound probe according to a modification example of Embodiment 1 of the invention.

In Embodiment 1, although the waterproof packing P1 is fixed to the cover rib CL1 of the battery cover 14, the waterproof packing P1 may be fixed to the sidewall 18B of the battery accommodation portion 18 of the housing body 13. For example, as shown in FIG. 7, the waterproof packing P1 is fixed to the inner wall surface WS1 of the sidewall 18B of the battery accommodation portion 18. In a state in which the cover rib CL1 is attached to the housing body 13, the waterproof packing P1 is elastically compressed between the inner wall surface WS1 of the sidewall 18B of the battery accommodation portion 18 and the outer peripheral surface PS1 of the cover rib CL1, and is closely attached to the outer peripheral surface PS1 of the cover rib CL1. Even in this case, similarly to a case where the waterproof packing P1 is fixed to the cover rib CL1, it is possible to dispose the battery 16 to be replaceable while securing a waterproof property for the battery 16.

Figure 8:
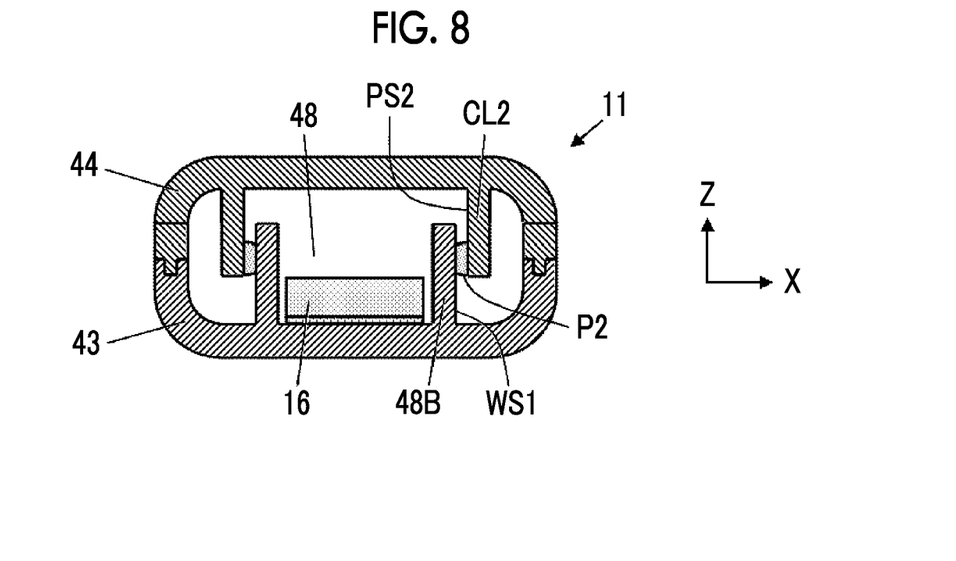
FIG. 8 is a cross-sectional view of an ultrasound probe according to another modification example of Embodiment 1 of the invention.

In Embodiment 1, as shown in FIG. 4, although the cover rib CL1 of the battery cover 14 is disposed more inside the battery accommodation portion 18 than the sidewall 18B of the battery accommodation portion 18, the cover rib CL1 may be disposed outside the battery accommodation portion 18. For example, as shown in FIG. 8, a cover rib CL2 of a battery cover 44 is disposed more outside a battery accommodation portion 48 than a sidewall 48B of the battery accommodation portion 48 of a housing body 43, and a waterproof packing P2 is fixed to an inner peripheral surface PS2 of the cover rib CL2. For this reason, the waterproof packing P2 is elastically compressed between the inner peripheral surface PS2 of the cover rib CL2 and an outer wall surface WS2 of the sidewall 48B of the battery accommodation portion 48, and is closely attached to the outer wall surface WS2 of the sidewall 48B of the battery accommodation portion 48. Even in this case, as shown in FIG. 4, similarly to a case where the cover rib CL1 of the battery cover 14 is disposed more inside the battery accommodation portion 18 than the sidewall 18B of the battery accommodation portion 18, it is possible to dispose the battery 16 to be replaceable while securing a waterproof property for the battery 16.

In Embodiment 1, although the battery 16 is fixed to the battery fixing surface 18A of the battery accommodation portion 18 by a double-sided tape T, a fixing method of the battery 16 is not particularly limited as long as the battery 16 is attachable and detachable. For example, though not shown, a mechanism that mechanically fixes the battery 16 to the battery accommodation portion 18, for example, a pressing portion for fixing the battery 16 to the sidewall 18B of the battery accommodation portion 18 can be provided. For example, the battery 16 may be fixed into the battery accommodation portion 18 by disposing a buffer material between the battery 16 and the battery cover 14.

In Embodiment 1, although the battery accommodation portion 18 has the sidewall 18B protruding from the battery fixing surface 18A, and the waterproof packing P1 is elastically compressed between the cover rib CL1 of the battery cover 14 and the sidewall 18B of the battery accommodation portion 18, and restrains water from entering the battery accommodation portion 18, for example, a pair of first side portions 17A and a pair of second side portions 17B of the recess portion 17 of the housing body 13 can be used as a sidewall of the battery accommodation portion 18 instead of providing the plate-shaped sidewall 18B. That is, in this case, the battery accommodation portion 18 is the recess portion 17 formed in the housing body 13, and the sidewall 18B of the battery accommodation portion 18 constitutes the first side portions 17A and the second side portions 17B of the recess portion 17.

In this case, the waterproof packing P1 is elastically compressed between the cover rib CL1 of the battery cover 14 and the first side portions 17A and between the cover rib CL1 and the second side portions 17B, thereby restraining water from entering the battery accommodation portion 18.

Embodiment 2

In Embodiment 1, the battery cover 14 is attached to the side surface of the housing body 13. In contrast, for example, the battery cover 14 may be attached to an end portion of the housing body 13 in the −Y direction.

Figure 9:
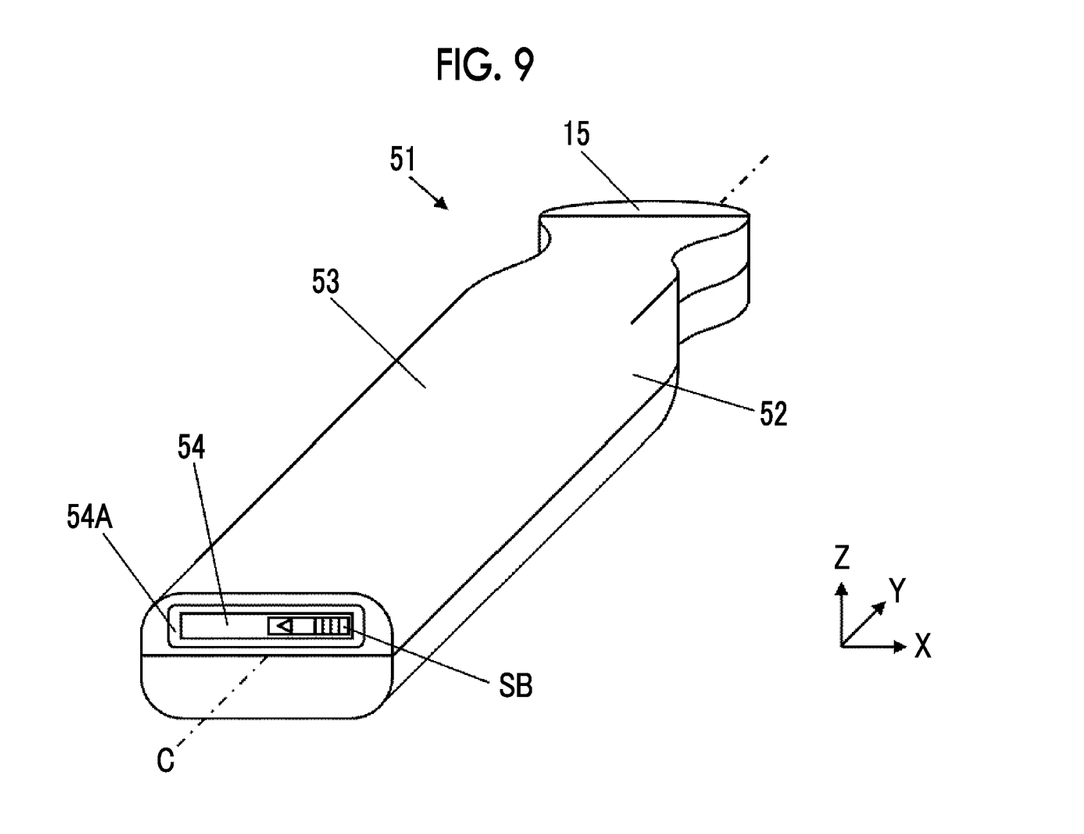
FIG. 9 is a perspective view of an ultrasound probe according to Embodiment 2 of the invention.

FIG. 9 shows an ultrasound probe 51 according to Embodiment 2 of the invention. As shown in FIG. 9, the ultrasound probe 51 has a housing 52 having a substantially prismatic shape around the center axis C, and a transducer array 15 disposed in an end portion of the housing 52 in the +Y direction. The housing 52 has a housing body 53 and a battery cover 54 attachably and detachably attached to the end portion of the housing body 53 in the −Y direction. Though not shown, the housing body 53 has a battery accommodation portion that accommodates a battery 16, and the battery cover 54 is attached to the housing body 53 to cover the battery accommodation portion.

The battery cover 54 has a slide button SB in a cover upper surface 54A constituting a part of the end portion of the housing body 53 in the −Y direction, fixing of the battery cover 54 and release of fixing of the battery cover 54 are made by an operation of the slide button SB. For example, the battery cover 54 can be fixed to the housing body 53 by sliding the slide button SB in the +X direction as shown in FIG. 9. A state in which the battery cover 54 is fixed to the housing body 53 can be released by sliding the slide button SB in the −X direction and the battery cover 54 can be detached from the housing body 53.

Figure 10:
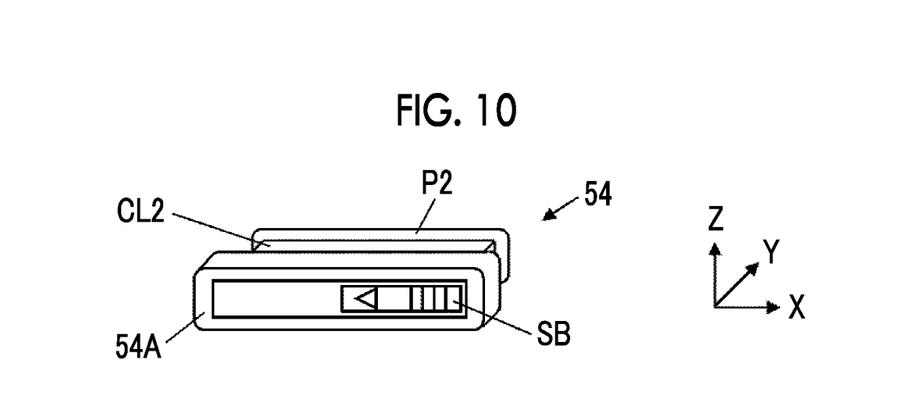
FIG. 10 is a perspective view of a battery cover as viewed from a front side in Embodiment 2 of the invention.
Figure 11:
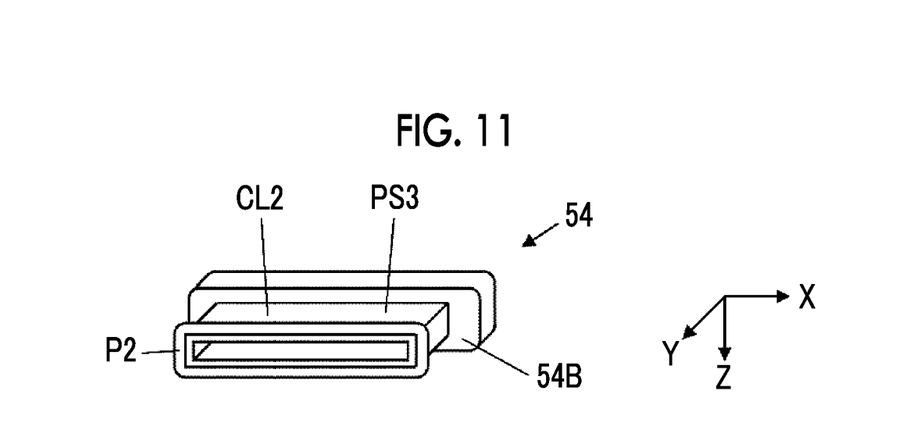
FIG. 11 is a perspective view of the battery cover as viewed from a rear side in Embodiment 2 of the invention.

As shown in FIG. 10, the battery cover 54 has a cover rib CL2 that protrudes in the +Y direction, and a waterproof packing P2 attached to the cover rib CL2. As shown in FIG. 11, the battery cover 54 has a cover lower surface 54B that is directed in an opposite direction to the cover upper surface 54A, and the cover rib CL2 protrudes in the +Y direction from the cover lower surface 54B. The cover rib CL2 has a closed plate shape having four sides of a pair of sides extending in the X direction and a pair of sides extending in the Z direction, and the waterproof packing P2 is fixed over the whole periphery of an outer peripheral surface PS3 of the cover rib CL2.

Though not shown, in a state in which the battery cover 54 is attached to the housing body 53, the waterproof packing P2 is elastically compressed between the outer peripheral surface PS3 of the cover rib CL2 and a sidewall portion of the battery accommodation portion, and is closely attached to the outer peripheral surface PS3 of the cover rib CL2 and the sidewall portion of the battery accommodation portion. For this reason, water is restrained from entering the battery accommodation portion from between the housing body 53 and the battery cover 54.

From the above, with the ultrasound probe 51 according to Embodiment 2, even though the battery cover 54 is attached to the end portion of the housing body 53 in the −Y direction, similarly to the ultrasound probe 11 of Embodiment 1, it is possible to dispose the battery 16 to be replaceable while securing a waterproof property for the battery 16.

Figure 12:
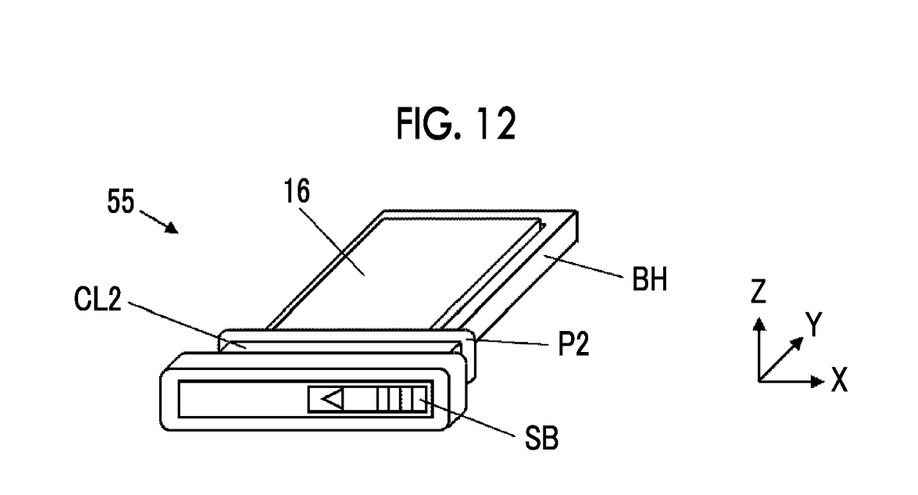
FIG. 12 is a perspective view of a battery cover in a modification example of Embodiment 2 of the invention.

A battery cover 55 shown in FIG. 12 may be attached to the housing body 53 instead of attaching the battery cover 54 to the housing body 53 in Embodiment 2. The battery cover 55 has a battery retention portion BH for disposing the battery 16 in the battery cover 54 shown in FIGS. 9 to 11. As shown in FIG. 12, in a state in which the battery 16 is disposed in the battery retention portion BH, it is possible to more easily perform attachment and detachment of the battery 16 to and from the ultrasound probe 51 by performing attachment and detachment of the battery cover 55 to and from the housing body 53.

Embodiment 3

Figure 13:
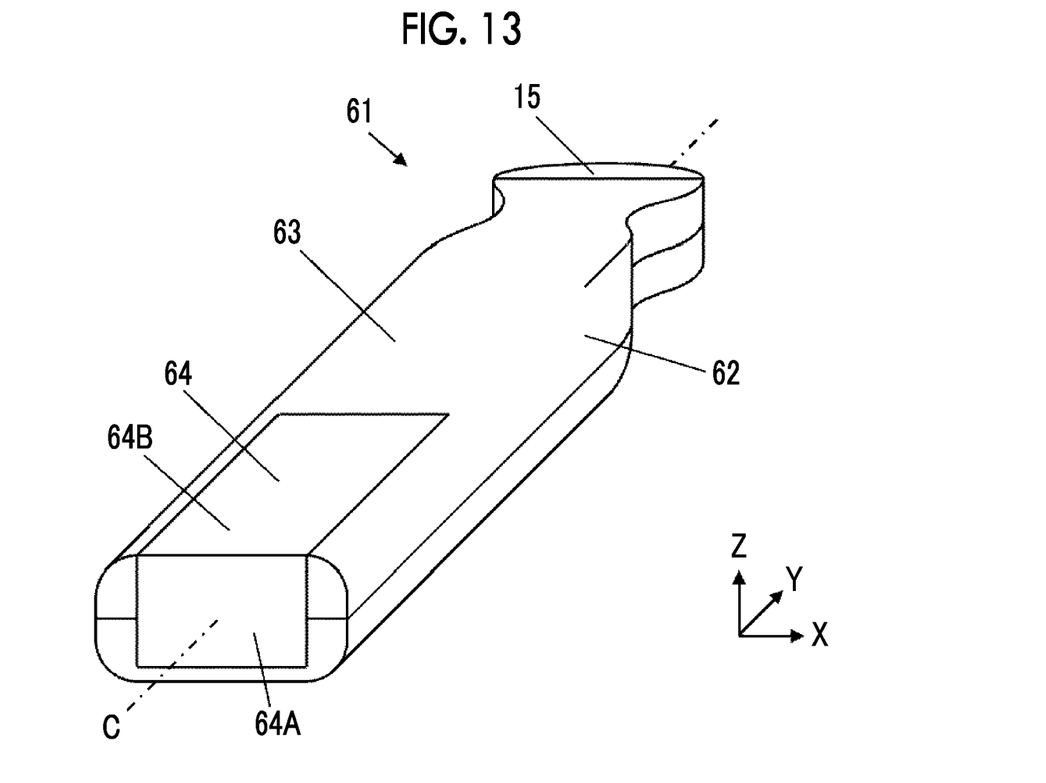
FIG. 13 is a perspective view of an ultrasound probe according to Embodiment 3 of the invention.

FIG. 13 shows an ultrasound probe 61 according to Embodiment 3. As shown in FIG. 13, the ultrasound probe 61 has a housing 62 having a substantially prismatic shape around a center axis Cl, and a transducer array 15 disposed in an end portion of the housing 62 in the +Y direction. The housing 62 has a housing body 63 and a battery cover 64 attachably and detachably attached to the housing body 63. Though not shown, the housing body 63 has a battery accommodation portion that accommodates a battery 16, and the battery cover 64 is attached to the housing body 63 to cover the battery accommodation portion. The battery cover 64 has an L shape, and has a first cover upper surface 64A that is parallel to an XZ plane and constitutes a part of an end portion of the housing 62 in the −Y direction, and a second cover upper surface 64B that is parallel to an XY plane and constitutes a part of a side surface of the housing 62.

Figure 14:
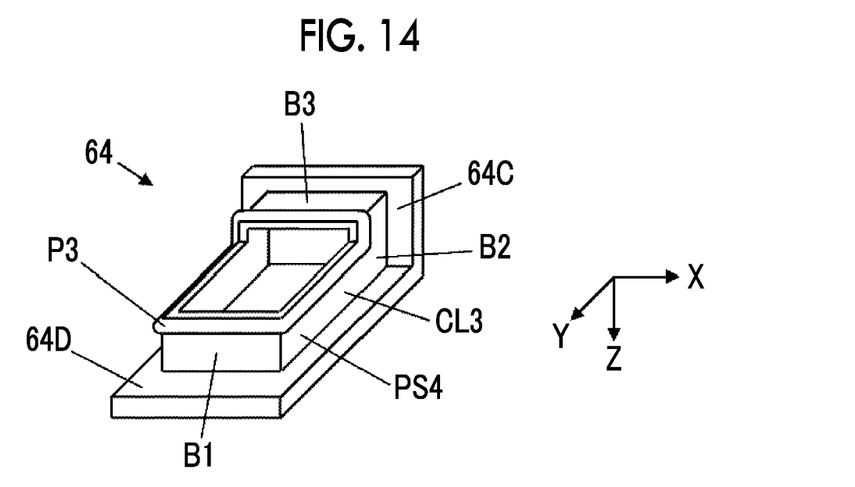
FIG. 14 is a perspective view of a battery cover as viewed from a rear side in Embodiment 3 of the invention.

As shown in FIG. 14, the battery cover 64 has a first cover lower surface 64C that is parallel to the XZ plane and is directed in an opposite direction to the first cover upper surface 64A, and a second cover lower surface 64D that is parallel to the XY plane and is directed in an opposite direction to the second cover upper surface 64B. The battery cover 64 has a cover rib CL3 that protrudes vertically in the +Y direction and the −Z direction from the first cover lower surface 64C and the second cover lower surface 64D, respectively, and a waterproof packing P3 fixed to the cover rib CL3.

As shown in FIG. 14, the cover rib CL3 has a closed plate shape in which a first plate portion B1 parallel to the XZ plane, a pair of so-called L-shaped second plate portions B2, which is parallel to a YZ plane and extends in the Z direction and the Y direction along the first cover lower surface 64C and the second cover lower surface 64D, and a third plate portion B3 parallel to the XY plane are connected to one another. The waterproof packing P3 is fixed over the whole periphery of an outer peripheral surface PS4 of the cover rib CL3.

Though not shown, in a state in which the battery cover 64 is attached to the housing body 63, the waterproof packing P3 is elastically compressed between the outer peripheral surface PS4 of the cover rib CL3 and the sidewall portion of the battery accommodation portion of the housing body 63. Thereby, the waterproof packing P3 is closely attached to the outer peripheral surface PS4 of the cover rib CL3 and the sidewall portion of the battery accommodation portion. For this reason, water is restrained from entering the battery accommodation portion from between the housing body 63 and the battery cover 64.

From the above, with the ultrasound probe 61 according to Embodiment 3, even though the battery cover 64 has a so-called L shape, similarly to the ultrasound probe 11 of Embodiment 1, it is possible to dispose the battery 16 to be replaceable while securing a waterproof property for the battery 16.

EXPLANATION OF REFERENCES

1: ultrasound diagnostic apparatus
11, 51, 61: ultrasound probe
12, 52, 62: housing
13, 43, 53, 63: housing body
14, 44, 54, 55, 64: battery cover
14A, 54A: cover upper surface
14B, 54B: cover lower surface
16: battery
17: recess portion
17A: first side portion
17B: second side portion
18, 48: battery accommodation portion
18A: battery fixing surface
18B, 48B: sidewall
15: transducer array
21: transmission unit
22: reception unit
23: ultrasound transmission and reception controller
24, 32: wireless communication unit
25, 37: communication controller
26: probe controller
27: ultrasound probe-side processor
28: amplification unit
29: AD conversion unit
30: beamformer
33: signal processing unit
34: image processing unit
35: display controller
36: display unit
38: body controller
39: operating unit
40: storage unit
41: diagnostic apparatus body-side processor
64A: first cover upper surface
64B: second cover upper surface
64C: first cover lower surface
64D: second cover lower surface
B1: first plate portion
B2: second plate portion
B3: third plate portion
C: center axis
CL1, CL2, CL3: cover rib
CP: hook portion
D: insertion hole
H: through-hole
P1, P2, P3: waterproof packing
PS1, PS3, PS4: outer peripheral surface
PS2: inner peripheral surface
S: screw
SB: slide button
T: double-sided tape
BH: battery retention portion
WS1: inner wall surface
WS2: outer wall surface.

What is claimed is:

1. An ultrasound probe comprising:
a transducer array;
a housing body having a battery accommodation portion;
a battery that is accommodated in the battery accommodation portion of the housing body;
a battery cover that is attachably and detachably mounted on the housing body to cover the battery accommodation portion and has an inner surface facing the battery accommodation portion and a cover rib protruding from the inner surface toward the battery accommodation portion; and
an elastically deformable waterproof packing that is disposed between a side surface of the cover rib of the battery cover and the housing body,
wherein the housing body has a recess portion,
the battery accommodation portion has a battery fixing surface which constitutes a bottom portion of the recess portion and to which the battery is fixed, and a sidewall which is surrounded by a side portion of the recess portion and protrudes from the battery fixing surface toward the battery cover,
a void portion is formed between the battery accommodation portion and the side portion of the recess portion,
the cover rib is apart from the side portion of the recess portion and the battery fixing surface,
the sidewall is apart from the inner surface of the battery cover, and
the waterproof packing is elastically compressed between the side surface of the cover rib and the sidewall of the battery accommodation portion, and restrains water from entering the battery accommodation portion from between the housing body and the battery cover.

2. The ultrasound probe according to claim 1,
wherein the cover rib has a closed shape extending along a whole periphery of the battery accommodation portion, and
the waterproof packing is disposed along a whole periphery of the cover rib.

3. The ultrasound probe according to claim 1,
wherein the cover rib is surrounded by the sidewall of the battery accommodation portion, and
the waterproof packing is elastically compressed between the side surface of the cover rib and an inner wall surface of the sidewall of the battery accommodation portion.

4. The ultrasound probe according to claim 3,
wherein the battery is fixed to the battery fixing surface by a double-sided tape.

5. The ultrasound probe according to claim 1,
wherein the cover rib surrounds the sidewall of the battery accommodation portion, and
the waterproof packing is elastically compressed between the side surface of the cover rib and an outer wall surface of the sidewall of the battery accommodation portion.

6. The ultrasound probe according to claim 5,
wherein the battery is fixed to the battery fixing surface by a double-sided tape.

7. The ultrasound probe according to claim 1,
wherein the battery is fixed to the battery fixing surface by a double-sided tape.

8. The ultrasound probe according to claim 1,
wherein the waterproof packing is fixed to the side surface of the cover rib.

9. The ultrasound probe according to claim 1,
wherein the housing body has a prismatic or columnar shape extending along a center axis, and
the transducer array is disposed at one end of the housing body along the center axis.

10. The ultrasound probe according to claim 9,
wherein the battery cover extends in parallel with the center axis and is disposed on a side surface of the housing body.

11. The ultrasound probe according to claim 9,
wherein the battery cover is disposed at the other end of the housing body along the center axis.

12. The ultrasound probe according to claim 1,
wherein the waterproof packing is formed of silicone rubber or fluororubber.

* * * * *